United States Patent
Xie et al.

(10) Patent No.: US 12,201,665 B2
(45) Date of Patent: Jan. 21, 2025

(54) POLYGONI MILLETII RHIZOME COMPOSITIONS AND METHODS OF PREPARING THE SAME

(71) Applicant: SHAANXI PANLONG PHARMACEUTICAL CO., LTD., Xi'an (CN)

(72) Inventors: Xiaolin Xie, Xi'an (CN); Dezhu Zhang, Xi'an (CN); Chengyuan Liang, Xi'an (CN); Shujun Ding, Xi'an (CN); Yuzhi Liu, Xi'an (CN); Zhao Ma, Xi'an (CN); Xuhua Zhou, Xi'an (CN); Zhong Meng, Xi'an (CN); Jianguo Meng, Xi'an (CN)

(73) Assignee: SHAANXI PANLONG PHARMACEUTICAL CO., LTD., Shaanxi (CN)

( * ) Notice: Subject to any disclaimer, the term of this patent is extended or adjusted under 35 U.S.C. 154(b) by 0 days.

(21) Appl. No.: 17/810,363

(22) Filed: Jul. 1, 2022

(65) Prior Publication Data
US 2023/0022609 A1  Jan. 26, 2023

(30) Foreign Application Priority Data

Jul. 14, 2021 (CN) .......................... 202110797470.5
Jul. 14, 2021 (CN) .......................... 202110797477.7

(51) Int. Cl.
| | | |
|---|---|---|
| A61K 36/704 | (2006.01) | |
| A61K 9/70 | (2006.01) | |
| A61K 36/13 | (2006.01) | |
| A61K 36/185 | (2006.01) | |
| A61K 36/21 | (2006.01) | |
| A61K 36/232 | (2006.01) | |
| A61K 36/24 | (2006.01) | |
| A61K 36/254 | (2006.01) | |
| A61K 36/258 | (2006.01) | |
| A61K 36/285 | (2006.01) | |
| A61K 36/286 | (2006.01) | |
| A61K 36/324 | (2006.01) | |
| A61K 36/328 | (2006.01) | |
| A61K 36/35 | (2006.01) | |
| A61K 36/36 | (2006.01) | |
| A61K 36/515 | (2006.01) | |
| A61K 36/537 | (2006.01) | |
| A61K 36/714 | (2006.01) | |
| A61K 36/83 | (2006.01) | |
| A61K 36/87 | (2006.01) | |
| A61K 36/88 | (2006.01) | |
| A61K 47/10 | (2017.01) | |
| A61K 47/14 | (2017.01) | |
| A61K 47/36 | (2006.01) | |
| A61K 47/38 | (2006.01) | |

(52) U.S. Cl.
CPC .......... *A61K 36/704* (2013.01); *A61K 9/7007* (2013.01); *A61K 36/13* (2013.01); *A61K 36/185* (2013.01); *A61K 36/21* (2013.01); *A61K 36/232* (2013.01); *A61K 36/24* (2013.01); *A61K 36/254* (2013.01); *A61K 36/258* (2013.01); *A61K 36/285* (2013.01); *A61K 36/286* (2013.01); *A61K 36/324* (2013.01); *A61K 36/328* (2013.01); *A61K 36/35* (2013.01); *A61K 36/36* (2013.01); *A61K 36/515* (2013.01); *A61K 36/537* (2013.01); *A61K 36/714* (2013.01); *A61K 36/83* (2013.01); *A61K 36/87* (2013.01); *A61K 36/88* (2013.01); *A61K 47/10* (2013.01); *A61K 47/14* (2013.01); *A61K 47/36* (2013.01); *A61K 47/38* (2013.01); *A61K 2236/333* (2013.01)

(58) Field of Classification Search
None
See application file for complete search history.

(56) References Cited

U.S. PATENT DOCUMENTS

2017/0095443 A1   4/2017   Luo

FOREIGN PATENT DOCUMENTS

| CN | 1718211 A | * | 1/2006 |
| CN | 102441113 A | | 5/2012 |

OTHER PUBLICATIONS

Singhuber, J., et al., Aconitum in Traditional Chinese Medicine—A valuable drug or an unpredictable risk?, J. Ethnopharmacology 126 (2009) 18-30 (Year: 2009).*

\* cited by examiner

*Primary Examiner* — H. Sarah Park

(57) ABSTRACT

A method of preparing a Polygoni Milletii Rhizome tincture includes: preparing a first mixture; extracting the first mixture with 70-90% ethanol under reflux condition to obtain a first extract solution; preparing a second mixture; extracting the second mixture with 50-70% ethanol to obtain a second extract solution; and mixing the first extract solution with the second extract solution to obtain the polygoni milletii rhizome tincture. A method of preparing a Polygoni Milletii Rhizome poultice includes: reparing a Polygoni Milletii Rhizome mixture; mixing the Polygoni Milletii Rhizome mixture and a skin penetration enhancer in water; mixing a moisturizing agent and a binder in water; adding a thickener in water; mixing methylparaben and ethylparaben in 90% ethanol; mixing all solutions to form a mixture; and applying the mixture on a non-woven fabric cloth and drying to form the Polygoni Milletii Rhizome poultice.

3 Claims, No Drawings

POLYGONI MILLETII RHIZOME COMPOSITIONS AND METHODS OF PREPARING THE SAME

The present application claims priority to Chinese Patent Application Nos. 202110797470.5, filed on Jul. 14, 2021, and 202110797477.7, filed on Jul. 14, 2021, both of which are incorporated by reference for all purposes as if fully set forth herein.

TECHNICAL FIELD

The invention relates to the technical field of traditional Chinese medicine compositions and methods of preparing the same, in particular to a Polygoni Milletii Rhizome tincture, a Polygoni Milletii Rhizome poultice, and methods of preparing the same.

BACKGROUND TECHNIQUE

Polygoni Milletii Rhizome tablet has a small drug load and low bioavailability after oral administration. There is a need for Polygoni Milletii Rhizome compositions with high bioavailability.

SUMMARY OF THE INVENTION

In one embodiment, the present application discloses a method of preparing a Polygoni Milletii Rhizome tincture. The method includes: mixing 10-20 parts by mass of Polygoni Milletii Rhizome, 10-20 parts by mass of Gentianae Macrophyllae Radix, 5-10 parts by mass of Achyranthis Bidentatae Radix, 20-30 parts by mass of Salviae Miltiorrhizae Radix Et Rhizoma, 10-20 parts by mass of Acanthopanacis Cortex, 5-10 parts by mass of Valerianae Officinalis Rhizoma Et Radix, 5-10 parts by mass of Sambuci Rhizoma, and 5-10 parts by mass of Ampelopsis Humulifoliae Cortex to form a first mixture; extracting the first mixture with 70-90% ethanol under reflux condition to obtain a first extract solution; mixing 30-50 parts by mass of Angelicae Sinensis Radix, 20-30 parts by mass of Paridis Rhizoma, 1-3 parts by mass of Qingwaqi (*Iris tectorum* Maxim.), 1-3 parts by mass of Aconiti Radix, 1-3 parts by mass of Aconiti Kusnezoffii Radix, 1-3 parts by mass of Aconiti Penduli Radix, 1-3 parts by mass of *Panacis* Majoris Rhizoma, 5-10 parts by mass of Trachelospermi Caulisetfolium, 5-10 parts by mass of Aconitisungpanensis Radix, 5-10 parts by mass of Aucklandiae Radix, 5-10 parts by mass of Olibanum, 1-3 parts by mass of Daphnes Cortex, 1-5 parts by mass of Chloranthi Radix Et Rhizoma, 1-5 parts by mass of Hylomeconis Rhizoma, 10-20 parts by mass of Eucommiae Cortex, 5-10 parts by mass of Carthami Flos, 1-5 parts by mass of Silene Radix, 5-10 parts by mass of Myrrha, 1-5 parts by mass of Lycopodii Herba, 5-10 parts by mass of Polygoni Suffulti Rhizoma, and 5-10 parts by mass of Tupistrae Rhizoma to form a second mixture; extracting the second mixture with 50-70% ethanol to obtain a second extract solution; and mixing the first extract solution with the second extract solution to obtain the polygoni milletii rhizome tincture.

In another embodiment, the first extract solution and the second extract solution are mixed in a volume ratio of 2:3 to obtain the polygoni milletii rhizome tincture.

In another embodiment, the present application discloses a method of preparing a Polygoni Milletii Rhizome poultice. The method includes mixing 10-30 parts by mass of Polygoni Milletii Rhizome, 2-8 parts by mass of Silene Radix, 10-30 parts by mass of Acanthopanacis Cortex, 10-30 parts by mass of Eucommiae Cortex, 25-90 parts by mass of Angelicae *Sinensis* Radix, 1-4 parts by mass of *Panacis* Majoris Rhizoma, 1-4 parts by mass of Qingwaqi (*Iris tectorum* Maxim.), 5-15 parts by mass of Ampelopsis Humulifoliae Cortex, 10-30 parts by mass of Gentianae Macrophyllae Radix, 5-15 parts by mass of Aucklandiae Radix, 1-4 parts by mass of Daphnes Cortex, 5-15 parts by mass of Trachelospermi Caulisetfolium, 1-4 parts by mass of Aconiti Radix, 2-8 parts by mass of Chloranthi Radix Et Rhizoma, 1-4 parts by mass of Aconiti Penduli Radix, 1-4 parts by mass of Aconiti Kusnezoffii Radix, 2-8 parts by mass of Hylomeconis Rhizoma, 5-15 parts by mass of Polygoni Suffulti Rhizoma, 5-15 parts by mass of *Carthami* Flos, 5-15 parts by mass of Myrrha, 5-15 parts by mass of Tupistrae Rhizoma, 10-30 parts by mass of *Valerianae Officinalis* Rhizoma Et Radix, 2-8 parts by mass of Lycopodii Herba, 10-30 parts by mass of Achyranthis Bidentatae Radix, 15-40 parts by mass of Salviae Miltiorrhizae Radix Et Rhizoma, 5-15 parts by mass of Aconitisungpanensis Radix, 5-15 parts by mass of *Sambuci* Rhizoma, 15-40 parts by mass of Paridis Rhizoma, and 5-15 parts by mass of Olibanum to form a Polygoni Milletii Rhizome mixture; mixing the Polygoni Milletii Rhizome mixture and a skin penetration enhancer in water to form a first solution; mixing a moisturizing agent and a binder in water to form a second solution; adding a thickener in water to form a third solution; mixing methylparaben and ethylparaben in 90% ethanol to form a fourth solution; mixing the first solution, the second solution, the third solution, and the fourth solution to form a mixture; and applying the mixture on a non-woven fabric cloth and drying to form the Polygoni Milletii Rhizome poultice.

In another embodiment, the skin penetration enhancer is azone, oleic acid, or a mixture of azone and oleic acid; the moisturizing agent is glycerol, butylene glycol, or polyethylene glycol; the binder is sodium polyacrylate or kaolinite; and the thickener is sodium alginate, sodium carboxymethyl cellulose or sodium hydroxyethyl cellulose.

DETAILED DESCRIPTION

The present invention will be further described in detail below with reference to specific embodiments, which are to explain rather than limit the present invention.

Example 1

10 g of Polygoni Milletii Rhizome, 10 of Gentianae Macrophyllae Radix, 5 g of Achyranthis Bidentatae Radix, 20 g of Salviae Miltiorrhizae Radix Et Rhizoma, 10 g of Acanthopanacis Cortex, 5 g of *Valerianae Officinalis* Rhizoma Et Radix, 5 g of *Sambuci* Rhizoma, and 5 g of Ampelopsis Humulifoliae Cortex were mixed and grinded, passed throught a 20 mesh sieve, added to 1,200 mL of 70% ethanol, refluxed and extracted three times, 1 hour each time, filtered, cooled down, and after 24 hours, filtered to obtain 1,118 mL of first extract solution. 30 g of Angelicae Sinensis Radix, 20 g of Paridis Rhizoma, 1 g of Qingwaqi (Iris tectorum Maxim.), 1 g of Aconiti Radix, 1 g of Aconiti Kusnezoffii Radix, 1 g of Aconiti Penduli Radix, 1 g of *Panacis* Majoris Rhizoma, 5 g of Trachelospermi Caulisetfolium, 5 g of Aconitisungpanensis Radix, 5 g of Aucklandiae Radix, 5 g of Olibanum, 1 g of Daphnes Cortex, 1 g of Chloranthi Radix Et Rhizoma, 1 g of Hylomeconis Rhizoma, 10 g of Eucommiae Cortex, 5 g of *Carthami* Flos, 1 g of Silene Radix, 5 g of Myrrha, 1 g of Lycopodii Herba, 5 g of Polygoni Suffulti Rhizoma, and 5 g of Tupistrae Rhizoma were added to 1,800 mL 50% ethanol, refluxed and extracted three times, 1 hour each time, filtered, cooled down, and after 24 hours, filtered to obtain 1,695 mL of second extract solution. The first extract solution and the second extract solution were mixed in a volume ratio of 2:3 to obtain 2,795 mL of polygoni milletii rhizome tincture.

Examples 2-5

Examples 2-5 were prepared in the same way as Example 1 but with diferent components as shown in the following table 1.

TABLE 1

|  | Example 2 | Example 3 | Example 4 | Example 5 |
|---|---|---|---|---|
| First Extract Solution |  |  |  |  |
| Polygoni Milletii Rhizome | 16.7 g | 20 g | 16.7 g | 20 g |
| Gentianae Macrophyllae Radix | 16.7 g | 20 g | 16.7 g | 20 g |
| Achyranthis Bidentatae Radix | 8.3 g | 10 g | 8.3 g | 10 g |
| Salviae Miltiorrhizae Radix Et Rhizoma | 25 g | 30 g | 25 g | 30 g |
| Acanthopanacis Cortex | 16.7 g | 20 g | 16.7 g | 20 g |
| Valerianae Officinalis Rhizoma Et Radix | 8.3 g | 10 g | 8.3 g | 10 g |
| Sambuci Rhizoma | 8.3 g | 10 g | 8.3 g | 10 g |
| Ampelopsis Humulifoliae Cortex | 8.3 g | 10 g | 8.3 g | 10 g |
| Second Extract Solution |  |  |  |  |

TABLE 1-continued

|  | Example 2 | Example 3 | Example 4 | Example 5 |
|---|---|---|---|---|
| Angelicae Sinensis Radix | 41.7 g | 50 g | 50 g | 41.7 g |
| Paridis Rhizoma | 25 g | 30 g | 30 g | 25 g |
| Qingwaqi (*Iris tectorum* Maxim.) | 1.7 g | 3 g | 3 g | 1.7 g |
| Aconiti Radix | 1.7 g | 3 g | 3 g | 1.7 g |
| Aconiti Kusnezoffii Radix | 1.7 g | 3 g | 3 g | 1.7 g |
| Aconiti Penduli Radix | 1.7 g | 3 g | 3 g | 1.7 g |
| Panacis Majoris Rhizoma, | 1.7 g | 3 g | 3 g | 1.7 g |
| Trachelospermi Caulisetfolium, | 8.3 g | 10 g | 10 g | 8.3 g |
| Aconitisungpanensis Radix | 8.3 g | 10 g | 10 g | 8.3 g |
| Aucklandiae Radix | 8.3 g | 10 g | 10 g | 8.3 g |
| Olibanum | 8.3 g | 10 g | 10 g | 8.3 g |
| Daphnes Cortex | 8.3 g | 10 g | 10 g | 8.3 g |
| Chloranthi Radix Et Rhizoma | 1.7 g | 5 g | 5 g | 1.7 g |
| Hylomeconis Rhizoma | 1.7 g | 5 g | 5 g | 1.7 g |
| Eucommiae Cortex | 16.7 g | 20 g | 20 g | 16.7 g |
| Carthami Flos | 8.3 g | 10 g | 10 g | 8.3 g |
| Silene Radix | 3.3 g | 5 g | 5 g | 3.3 g |
| Myrrha | 8.3 g | 10 g | 10 g | 8.3 g |
| Lycopodii Herba | 3.3 g | 5 g | 5 g | 3.3 g |
| Polygoni Suffulti Rhizoma, | 8.3 g | 10 g | 10 g | 8.3 g |
| Tupistrae Rhizoma | 8.3 g | 10 g | 10 g | 8.3 g |

Comparative Examples 1-6

Comparative Examples 2-6 were prepared in the same way as Example 1 but with different components as shown in the following table 2.

TABLE 2

|  | Comparative Example 1 | Comparative Example 2 | Comparative Example 3 | Comparative Example 4 | Comparative Example 5 | Comparative Example 6 |
|---|---|---|---|---|---|---|
| First Extract Solution |  |  |  |  |  |  |
| Polygoni Milletii Rhizome | — | 16.7 g | 16.7 g | 16.7 g | 16.7 g | 16.7 g |
| Gentianae Macrophyllae Radix | 16.7 g | 16.7 g | 16.7 g | — | 16.7 g | 16.7 g |
| Achyranthis Bidentatae Radix | 8.3 g | 8.3 g | — | 8.3 g | 8.3 g | 8.3 g |
| Salviae Miltiorrhizae Radix Et Rhizoma | 25 g | — | 25 g | 25 g | 25 g | 25 g |
| Acanthopanacis Cortex | 16.7 g | 16.7 g | 16.7 g | 16.7 g | — | 16.7 g |
| Valerianae Officinalis Rhizoma Et Radix | 8.3 g | 8.3 g | 8.3 g | 8.3 g | — | 8.3 g |
| Sambuci Rhizoma | 8.3 g | 8.3 g | 8.3 g | 8.3 g | 8.3 g | 8.3 g |
| Ampelopsis Humulifoliae Cortex | 8.3 g | 8.3 g | 8.3 g | 8.3 g | 8.3 g | 8.3 g |
| Second Extract Solution |  |  |  |  |  |  |
| Angelicae Sinensis Radix | 41.7 g | — | 41.7 g | 41.7 g | 41.7 g | 41.7 g |
| Paridis Rhizoma | 25 g | 25 g | — | 25 g | 25 g | 25 g |
| Qingwaqi (*Iris tectorum* Maxim.) | 1-7 g | 1-7 g | 1-7 g | 1-7 g | 1-7 g | 1-7 g |
| Aconiti Radix | 1-7 g | 1-7 g | 1-7 g | 1-7 g | 1-7 g | — |
| Aconiti Kusnezoffii Radix | 1-7 g | 1-7 g | 1-7 g | 1-7 g | 1-7 g | — |
| Aconiti Penduli Radix | 1-7 g | 1-7 g | 1-7 g | 1-7 g | 1-7 g | — |
| Panacis Majoris Rhizoma, | 1-7 g | 1-7 g | 1-7 g | 1-7 g | 1-7 g | 1-7 g |
| Trachelospermi Caulisetfolium, | 8.3 g | 8.3 g | 8.3 g | — | 8.3 g | 8.3 g |
| Aconitisungpanensis Radix | 8.3 g | 8.3 g | 8.3 g | 8.3 g | 8.3 g | 8.3 g |
| Aucklandiae Radix | 8.3 g | 8.3 g | 8.3 g | 8.3 g | 8.3 g | 8.3 g |
| Olibanum | 8.3 g | 8.3 g | 8.3 g | 8.3 g | 8.3 g | 8.3 g |
| Daphnes Cortex | 8.3 g | 8.3 g | 8.3 g | 8.3 g | 8.3 g | 8.3 g |

TABLE 2-continued

|  | Comparative Example 1 | Comparative Example 2 | Comparative Example 3 | Comparative Example 4 | Comparative Example 5 | Comparative Example 6 |
|---|---|---|---|---|---|---|
| Chloranthi Radix Et Rhizoma | 1-7 g | 1-7 g | 1-7 g | 1-7 g | 1-7 g | 1-7 g |
| Hylomeconis Rhizoma | 1-7 g | 1-7 g | 1-7 g | 1-7 g | 1-7 g | 1-7 g |
| Eucommiae Cortex | 16.7 g | 16.7 g | 16.7 g | 16.7 g | 16.7 g | 16.7 g |
| Carthami Flos | 8.3 g | 8.3 g | 8.3 g | 8.3 g | 8.3 g | 8.3 g |
| Silene Radix | 3.3 g | 3.3 g | 3.3 g | 3.3 g | 3.3 g | 3.3 g |
| Myrrha | 8.3 g | 8.3 g | 8.3 g | 8.3 g | 8.3 g | 8.3 g |
| Lycopodii Herba | 3.3 g | 3.3 g | 3.3 g | 3.3 g | 3.3 g | 3.3 g |
| Polygon! Suffulti Rhizoma, | 8.3 g | 8.3 g | 8.3 g | 8.3 g | 8.3 g | 8.3 g |
| Tupistrae Rhizoma | 8.3 g | 8.3 g | 8.3 g | 8.3 g | 8.3 g | 8.3 g |

Example 6

Analgesia experiment (twisting method) was conducted to determine the analgesic activity of the compositions of Examples 1-5 and Comparative Examples 1-6. The results are shown in Table 3.

TABLE 3

|  | Analgesia rate (%) |
|---|---|
| Example 1 | 54.2 |
| Example 2 | 60.5 |
| Example 3 | 60.8 |
| Example 4 | 61.8 |
| Example 5 | 64.4 |
| Comparative Example 1 | 52.7 |
| Comparative Example 2 | 46.5 |
| Comparative Example 3 | 42.9 |
| Comparative Example 4 | 41.8 |
| Comparative Example 5 | 40.0 |
| Comparative Example 6 | 30.7 |
| Control group (0.2% rotundine) | 81.5 |
| Normal saline |  |

Example 7

Anti-inflammatory experiment (mouse auricle swelling method) was conducted to mesure, the anti-inflammatory activity of the compositions of Examples 1-5 and Comparative Examples 1-6. The results are shown in Table 4.

TABLE 4

|  | Swelling inhibition rate (%) |
|---|---|
| Example 1 | 25.20 |
| Example 2 | 29.63 |
| Example 3 | 29.52 |
| Example 4 | 32.00 |
| Example 5 | 32.43 |
| Comparative Example 1 | 23.06 |
| Comparative Example 2 | 20.04 |
| Comparative Example 3 | 7.00 |
| Comparative Example 4 | 11.00 |
| Comparative Example 5 | 10.23 |
| Comparative Example 6 | 17.56 |
| Control group (aspirin) | 36.42 |
| Blank group |  |

Example 8

Anti-arthritis experiment (thirty-nine volunteers: 15 males and 14 females, divided into 13 groups.) was conducted to measure the anti-arthritis activities.

For the patients treated with the compositions of Examples 1-5, the redness and swelling disappeared within 11 days after the medication, and the pain disappeared within 14 days, no recurrence within 30 days.

For the patients treated with the compositions of Comparative Examples 1-6, the redness and pain disappeared within 26 days after the medication, and the recurrence rate was 22.2% within 30 days.

Example 9

Polygoni Milletii Rhizome, Silene Radix, Acanthopanacis Cortex, Eucommiae Cortex, Angelicae *Sinensis* Radix, *Panacis* Majoris Rhizoma, Qingwaqi (*Iris tectorum* Maxim.), Ampelopsis Humulifoliae Cortex, Gentianae Macrophyllae Radix, Aucklandiae Radix, Daphnes Cortex, 5 Trachelospermi Caulisetfolium Aconiti Radix, Chloranthi Radix Et Rhizoma, Aconiti Penduli Radix, Aconiti Kusnezoffii Radix, Hylomeconis Rhizoma, Polygoni Suffulti Rhizoma, *Carthami* Flos, Myrrha, Tupistrae Rhizoma, *Valerianae Officinalis* Rhizoma Et Radix, Lycopodii Herba, Achyranthis Bidentatae Radix, Salviae Miltiorrhizae Radix Et Rhizoma were mixed in a ratio as shown in Table 5 to form a Polygoni Milletii Rhizome mixture;

TABLE 5

| Polygoni Milletii Rhizome | 10 g |
|---|---|
| Eucommiae Cortex | 10 g |
| Qingwaqi | 1 g |
| Aucklandiae Radix | 5 g |
| Aconiti Radix | 1 g |
| Aconiti Kusnezoffii Radix | 1 g |
| Carthami Flos | 5 g |
| Valerianae Officinalis Rhizoma Et Radix | 10 g |
| Salviae Miltiorrhizae Radix Et Rhizoma | 15 g |
| Paridis Rhizoma | 15 g |
| Silene Radix | 2 g |
| Angelicae Sinensis Radix | 25 g |
| Ampelopsis Humulifoliae Cortex | 5 g |
| Daphnes Cortex | 1 g |
| Chloranthi Radix Et Rhizoma | 2 g |
| Hylomeconis Rhizoma | 2 g |
| Myrrha | 5 g |
| Lycopodii Herba | 2 g |
| Aconitisungpanensis Radix | 5 g |
| Olibanum | 5 g |
| Acanthopanacis Cortex | 10 g |
| Panacis Majoris Rhizoma | 1 g |
| Gentianae Macrophyllae Radix | 10 g |
| Trachelospermi Caulisetfolium | 5 g |
| Aconiti Penduli Radix | 1 g |
| Polygoni Suffulti Rhizoma | 5 g |
| Tupistrae Rhizoma | 5 g |
| Achyranthis Bidentatae Radix | 10 g |

TABLE 5-continued

| | |
|---|---|
| Sambuci Rhizoma | 5 g |
| Total | 174 g |

Preparation of Polygoni Milletii Rhizome poultice:

(1) The Polygoni Milletii Rhizome mixture prepared above and 5 g of azone and oleic acid mixture (6:4) were added to 100 mL deionized water, and stirred to make evenly dispersed;

(2) 30 g of sodium polyacrylate was dispersed in 250 mL of glycerin, 420 mL of distilled water was added, and the mixture was stirred to make completely dissolved;

(3) 30 g of sodium alginate was dissolved in 150 mL of water, and let it stand overnight to fully swell and dissolve;

(4) 6 g of methylparaben and 6 g ethylparaben were dissolved in 70 mL of 90% ethanol to prepare a preservative solution;

(5) The solution of step (3) was added to the solution of (2), and the solution of step (1) and solution of step (4) were added consecutively to form a viscous fluid. The viscous fluid was immediately applied to 4 pieces of non-woven fabric cloth (55 cm*49 cm). The non-woven fabric cloth was dried in an oven at 40° C. The non-woven fabric cloth was cut into 70 pieces. Each piece contains 1.24 g of the Polygoni Milletii Rhizome poultice, which can effectively improve and treat arthritis.

Example 10

Polygoni Milletii Rhizome, Silene Radix, Acanthopanacis Cortex, Eucommiae Cortex, Angelicae *Sinensis* Radix, *Panacis* Majoris Rhizoma, Qingwaqi (*Iris tectorum* Maxim.), Ampelopsis Humulifoliae Cortex, Gentianae Macrophyllae Radix, Aucklandiae Radix, Daphnes Cortex, Trachelospermi Caulisetfolium Aconiti Radix, Chloranthi Radix Et Rhizoma, Aconiti Penduli Radix, Aconiti Kusnezoffii Radix, Hylomeconis Rhizoma, Polygoni Suffulti Rhizoma, *Carthami* Flos, Myrrha, Tupistrae Rhizoma, *Valerianae Officinalis* Rhizoma Et Radix, Lycopodii Herba, Achyranthis Bidentatae Radix, Salviae Miltiorrhizae Radix Et Rhizoma were mixed in a ratio as shown in Table 6 to form a Polygoni Milletii Rhizome mixture;

TABLE 6

| | |
|---|---|
| Polygoni Milletii Rhizome | 16.7 g |
| Eucommiae Cortex | 16.7 g |
| Qingwaqi | 1.7 g |
| Aucklandiae Radix | 8.3 g |
| Aconiti Radix | 1.7 g |
| Aconiti Kusnezoffii Radix | 1.7 g |
| Carthami Flos | 8.3 g |
| Valerianae Officinalis Rhizoma Et Radix | 16.7 g |
| Salviae Miltiorrhizae Radix Et Rhizoma | 25 g |
| Paridis Rhizoma | 25 g |
| Silene Radix | 3.8 g |
| Angelicae Sinensis Radix | 41.7 g |
| Ampelopsis Humulifoliae Cortex | 8.3 g |
| Daphnes Cortex | 1.7 g |
| Chloranthi Radix Et Rhizoma | 3.3 g |
| Hylomeconis Rhizoma | 3.3 g |
| Myrrha | 8.3 g |
| Lycopodii Herba | 3.3 g |
| Aconitisungpanensis Radix | 8.3 g |
| Olibanum | 8.3 g |
| Acanthopanacis Cortex | 16.7 g |
| Panacis Majoris Rhizoma | 1.7 g |
| Gentianae Macrophyllae Radix | 16.7 g |
| Trachelospermi Caulisetfolium | 8.3 g |
| Aconiti Penduli Radix | 1.7 g |

TABLE 6-continued

| | |
|---|---|
| Polygoni Suffulti Rhizoma | 8.3 g |
| Tupistrae Rhizoma | 8.3 g |
| Achyranthis Bidentatae Radix | 16.7 g |
| Sambuci Rhizoma | 8.3 g |
| Total | 298.3 g |

Preparation of Polygoni Milletii Rhizome poultice:

(1) The Polygoni Milletii Rhizome mixture prepared above and 10 g of azone and oleic acid mixture (6:4) were added to 100 mL deionized water, and stirred to make evenly dispersed;

(2) 40 g of sodium polyacrylate was dispersed in 270 mL of glycerin, 600 mL of distilled water was added, and the mixture was stirred to make completely dissolved;

(3) 40 g of sodium alginate was dissolved in 180 mL of water, and let it stand overnight to fully swell and dissolve;

(4) 12 g of methylparaben and 12 g ethylparaben were dissolved in 70 mL of 90% ethanol to prepare a preservative solution;

(5) The solution of step (3) was added to the solution of (2), and the solution of step (1) and solution of step (4) were added consecutively to form a viscous fluid. The viscous fluid was immediately applied to 4 pieces of non-woven fabric cloth (55 cm*49 cm). The non-woven fabric cloth was dried in an oven at 40° C. The non-woven fabric cloth was cut into 70 pieces. Each piece contains 2.05 g of the Polygoni Milletii Rhizome poultice, which can effectively improve and treat arthritis.

Example 11

Polygoni Milletii Rhizome, Silene Radix, Acanthopanacis Cortex, Eucommiae Cortex, Angelicae *Sinensis* Radix, *Panacis* Majoris Rhizoma, Qingwaqi (*Iris tectorum* Maxim.), Ampelopsis Humulifoliae Cortex, Gentianae Macrophyllae Radix, Aucklandiae Radix, Daphnes Cortex, Trachelospermi Caulisetfolium Aconiti Radix, Chloranthi Radix Et Rhizoma, Aconiti Penduli Radix, Aconiti Kusnezoffii Radix, Hylomeconis Rhizoma, Polygoni Suffulti Rhizoma, *Carthami* Flos, Myrrha, Tupistrae Rhizoma, *Valerianae Officinalis* Rhizoma Et Radix, Lycopodii Herba, Achyranthis Bidentatae Radix, Salviae Miltiorrhizae Radix Et Rhizoma were mixed in a ratio as shown in Table 7 to form a Polygoni Milletii Rhizome mixture;

TABLE 7

| | |
|---|---|
| Polygoni Milletii Rhizome | 30 g |
| Eucommiae Cortex | 30 g |
| Qingwaqi | 4 g |
| Aucklandiae Radix | 15 g |
| Aconiti Radix | 4 g |
| Aconiti Kusnezoffii Radix | 4 g |
| Carthami Flos | 15 g |
| Valerianae Officinalis Rhizoma Et Radix | 30 g |
| Salviae Miltiorrhizae Radix Et Rhizoma | 40 g |
| Paridis Rhizoma | 40 g |
| Silene Radix | 8 g |
| Angelicae Sinensis Radix | 90 g |
| Ampelopsis Humulifoliae Cortex | 15 g |
| Daphnes Cortex | 4 g |
| Chloranthi Radix Et Rhizoma | 8 g |
| Hylomeconis Rhizoma | 38 g |
| Myrrha | 15 g |
| Lycopodii Herba | 8 g |
| Aconitisungpanensis Radix | 15 g |
| Olibanum | 15 g |
| Acanthopanacis Cortex | 30 g |

TABLE 7-continued

| | |
|---|---|
| Panacis Majoris Rhizoma | 4 g |
| Gentianae Macrophyllae Radix | 30 g |
| Trachelospermi Caulisetfolium | 15 g |
| Aconiti Penduli Radix | 4 g |
| Polygoni Suffulti Rhizoma | 15 g |
| Tupistrae Rhizoma | 15 g |
| Achyranthis Bidentatae Radix | 30 g |
| Sambuci Rhizoma | 15 g |
| Total | 556 g |

Preparation of Polygoni Milletii Rhizome poultice:

(1) The Polygoni Milletii Rhizome mixture prepared above and 15 g of azone and oleic acid mixture (6:4) were added to 100 mL deionized water, and stirred to make evenly dispersed;

(2) 60 g of sodium polyacrylate was dispersed in 300 mL of glycerin, 800 mL of distilled water was added, and the mixture was stirred to make completely dissolved;

(3) 60 g of sodium alginate was dissolved in 210 mL of water, and let it stand overnight to fully swell and dissolve;

(4) 20 g of methylparaben and 20 g ethylparaben were dissolved in 70 mL of 90% ethanol to prepare a preservative solution;

(5) The solution of step (3) was added to the solution of (2), and the solution of step (1) and solution of step (4) were added consecutively to form a viscous fluid. The viscous fluid was immediately applied to 4 pieces of non-woven fabric cloth (55 cm*49 cm). The non-woven fabric cloth was dried in an oven at 40° C. The non-woven fabric cloth was cut into 70 pieces. Each piece contains 3.99 g of the Polygoni Milletii Rhizome poultice, which can effectively improve and treat arthritis.

Example 12

Example 12 was conducted in the same way as Example 10, except that 40 g of sodium polyacrylate was dispersed in 270 mL of butylene glycol (not glycerin). Each piece contains 2.06 g of the Polygoni Milletii Rhizome poultice, which can effectively improve and treat arthritis.

Example 13

Example 13 was conducted in the same way as Example 10, except that 40 g of sodium polyacrylate was dispersed in 270 mL of polyethylene glycol (not glycerin). Each piece contains 2.06 g of the Polygoni Milletii Rhizome poultice, which can effectively improve and treat arthritis.

Example 14

Example 14 was conducted in the same way as Example 10, except that 40 g of kaolinite (not sodium polyacrylate) was dispersed in 270 mL of glycerin. Each piece contains 2.05 g of the Polygoni Milletii Rhizome poultice, which can effectively improve and treat arthritis.

Example 15

Example 15 was conducted in the same way as Example 10, except that the Polygoni Milletii Rhizome mixture and 10 g of azone (not azone and oleic acid mixture) were added to 100 mL deionized water. Each piece contains 2.05 g of the Polygoni Milletii Rhizome poultice, which can effectively improve and treat arthritis.

Example 16

Example 16 was conducted in the same way as Example 10, except that the Polygoni Milletii Rhizome mixture and 10 g of oleic acid (not azone and oleic acid mixture) were added to 100 mL deionized water. Each piece contains 2.05 g of the Polygoni Milletii Rhizome poultice, which can effectively improve and treat arthritis.

Comparative Examples 7-13

Comparative Examples 7-13 were conducted in the same way Example 10, except Polygoni Milletii Rhizome was not added (Comparative Example 7), Paridis Rhizoma was not added (Comparative Example 8), Achyranthis Bidentatae Radix was not added (Comparative Example 9) Eucommiae Cortex was not added (Comparative Example 10), Acanthopanacis Cortex, Gentianae Macrophyllae Radix, and *Valerianae Officinalis* Rhizoma Et Radix were not added (Comparative Example 11), Salviae Miltiorrhizae Radix Et Rhizoma and Angelicae *Sinensis* Radix were not added (Comparative Example 12), and Aconiti Radix, Aconiti Kusnezoffii Radix, and Aconiti Penduli Radix were not added (Comparative Example 13).

Example 18

Analgesia experiment (twisting method) was conducted to determine the analgesic activity of the compositions of Examples 9-11 and 15-16 and Comparative Examples 7-13. The results are shown in Table 8.

TABLE 8

| | Analgesia rate (%) |
|---|---|
| Example 9 | 62.29 |
| Example 10 | 64.67 |
| Example 11 | 64.23 |
| Example 15 | 48.67 |
| Example 16 | 47.56 |
| Comparative Example 7 | 55.31 |
| Comparative Example 8 | 53.10 |
| Comparative Example 9 | 46.73 |
| Comparative Example 10 | 25.19 |
| Comparative Example 11 | 44.13 |
| Comparative Example 12 | 35.66 |
| Comparative Example 13 | 18.00 |
| Control group (ibuprofen cream) | 76.97 |
| Blank | |

Example 19

Anti-inflammatory experiment (mouse auricle swelling method) was conducted to mesure, the anti-inflammatory activity of the compositions of Examples 9-11 and 15-16 and Comparative Examples 7-13. The results are shown in Table 9.

TABLE 9

| | Swelling inhibition rate (%) |
|---|---|
| Example 9 | 33.04 |
| Example 10 | 36.72 |
| Example 11 | 37.40 |
| Example 15 | 23.84 |
| Example 16 | 21.61 |
| Comparative Example 1 | 29.07 |
| Comparative Example 2 | 18.41 |
| Comparative Example 3 | 14.63 |
| Comparative Example 4 | 27.03 |

TABLE 9-continued

| | Swelling inhibition rate (%) |
|---|---|
| Comparative Example 5 | 18.51 |
| Comparative Example 6 | 19.28 |
| Comparative Example 7 | 19.09 |
| Control group (ibuprofen cream) | 39.73 |
| Blank group | |

Example 20

Anti-arthritis experiment (forty-two volunteers: divided into 14 groups, 3 each group) was conducted to measure the anti-arthritis activities.

For the patients treated with the compositions of Examples 9-16, the redness and swelling disappeared within 11 days after the medication, and the pain disappeared within 21 days, no recurrence within 30 days.

For the patients treated with the compositions of Comparative Examples 7-13, the redness and pain disappeared within 28 days after the medication, and the recurrence rate was 47.6% within 30 days.

The above content is only to illustrate the technical idea of the present invention, and cannot limit the protection scope of the present invention. Any modification made on the basis of the technical solution proposed in accordance with the technical idea of the present invention falls within the scope of the claims of the present invention. within the scope of protection.

The invention claimed is:

1. A method of preparing a Polygoni Milletii Rhizome tincture comprising:
   mixing 10-20 parts by mass of Polygoni Milletii Rhizome, 10-20 parts by mass of Gentianae Macrophyllae Radix, 5-10 parts by mass of Achyranthis Bidentatae Radix, 20-30 parts by mass of Salviae Miltiorrhizae Radix Et Rhizoma, 10-20 parts by mass of Acanthopanacis Cortex, 5-10 parts by mass of Valerianae Officinalis Rhizoma Et Radix, 5-10 parts by mass of Sambuci Rhizoma, and 5-10 parts by mass of Ampelopsis Humulifoliae Cortex to form a first mixture;
   extracting the first mixture with 70-90% ethanol under reflux condition to obtain a first extract solution;
   mixing 30-50 parts by mass of Angelicae Sinensis Radix, 20-30 parts by mass of Paridis Rhizoma, 1-3 parts by mass of Qingwaqi (*Iris tectorum* Maxim.), 1-3 parts by mass of Aconiti Radix, 1-3 parts by mass of Aconiti Kusnezoffii Radix, 1-3 parts by mass of Aconiti Penduli Radix, 1-3 parts by mass of Panacis Majoris Rhizoma, 5-10 parts by mass of Trachelospermi Caulisetfolium, 5-10 parts by mass of Aconitisungpanensis Radix, 5-10 parts by mass of Aucklandiae Radix, 5-10 parts by mass of Olibanum, 1-3 parts by mass of Daphnes Cortex, 1-5 parts by mass of Chloranthi Radix Et Rhizoma, 1-5 parts by mass of Hylomeconis Rhizoma, 10-20 parts by mass of Eucommiae Cortex, 5-10 parts by mass of Carthami Flos, 1-5 parts by mass of Silene Radix, 5-10 parts by mass of Myrrha, 1-5 parts by mass of Lycopodii Herba, 5-10 parts by mass of Polygoni Suffulti Rhizoma, and 5-10 parts by mass of Tupistrae Rhizoma to form a second mixture;
   extracting the second mixture with 50-70% ethanol to obtain a second extract solution; and
   mixing the first extract solution with the second extract solution to obtain the Polygoni Milletii Rhizome tincture.

2. The method of claim 1, wherein the first extract solution and the second extract solution are mixed in a volume ratio of 2:3 to obtain the Polygoni Milletii Rhizome tincture.

3. A method of preparing a Polygoni Milletii Rhizome poultice comprising:
   mixing 30 g of Polygoni Milletii Rhizome, 8 g of Silene Radix, 30 g Acanthopanacis Cortex, 30 g Eucommiae Cortex, 90 g of Angelicae Sinensis Radix, 4 g of Panacis Majoris Rhizoma, 4 g of Iris tectorum Maxim (Qingwaqi), 15 g of Ampelopsis Humulifoliae Cortex, 30 g of Gentianae Macrophyllae Radix, 15 g of Aucklandiae Radix, 4 g of Daphnes Cortex, 15 g of Trachelospermi Caulisetfolium, 4 g of Aconiti Radix, 8 g of Chloranthi Radix Et Rhizoma, 4 g of Aconiti Penduli Radix, 4 g of Aconiti Kusnezoffii Radix, 38 g of Hylomeconis Rhizoma, 15 g of Polygoni Suffulti Rhizoma, 15 g of Carthami Flos, 15 g of Myrrha, 15 g of Tupistrae Rhizoma, 30 g of Valerianae Officinalis Rhizoma Et Radix, 8 g of Lycopodii Herba, 30 g of Achyranthis Bidentatae Radix, 40 g of Salviae Miltiorrhizae Radix Et Rhizoma, 15 g of Aconitum Sungpanense Radix, 15 g of Sambuci Rhizoma, 40 g of Paridis Rhizoma, and 15 g of Olibanum to obtain a Polygoni Milletii Rhizome mixture;
   mixing the Polygoni Milletii Rhizome mixture, 15 g of an azone and oleic acid mixture, and 100 mL water to obtain a first solution;
   mixing 60 g of sodium polyacrylate, 300 mL of glycerin, 800 mL of water to obtain a second solution;
   mixing 60 g of sodium alginate and 210 mL of water to obtain a third solution;
   mixing 20 g of methylparaben, 20 g of ethylparaben, and 70 mL of 90% ethanol to obtain a preservative solution;
   adding the third solution to the second solution;
   adding the first solution and the preservative solution consecutively to the second solution to form a viscous fluid;
   applying the viscous fluid to a non-woven fabric cloth; and
   drying the non-woven fabric cloth to form the Polygoni Milletii Rhizome poultice.

* * * * *